(12) United States Patent
Bonjouklian et al.

(10) Patent No.: US 7,037,921 B2
(45) Date of Patent: May 2, 2006

(54) COMPOUNDS AND METHODS FOR INHIBITING MRP1

(75) Inventors: Rosanne Bonjouklian, Zionsvill, IN (US); Louis Nickolaus Jungheim, Indianapolis, IN (US); Kenneth Jeff Thrasher, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 294 days.

(21) Appl. No.: 10/473,241

(22) PCT Filed: Mar. 28, 2002

(86) PCT No.: PCT/US02/06668

§ 371 (c)(1),
(2), (4) Date: Sep. 25, 2003

(87) PCT Pub. No.: WO02/081482

PCT Pub. Date: Oct. 17, 2002

(65) Prior Publication Data

US 2004/0097507 A1     May 20, 2004

Related U.S. Application Data

(60) Provisional application No. 60/282,641, filed on Apr. 9, 2001.

(51) Int. Cl.
*C07D 498/12* (2006.01)
*A61K 31/435* (2006.01)

(52) U.S. Cl. ......................................... 514/293; 546/83
(58) Field of Classification Search ................. 546/83; 514/293

See application file for complete search history.

(56) References Cited

FOREIGN PATENT DOCUMENTS

WO   WO99/51227 A   10/1999
WO   WO99/51228 A   10/1999

*Primary Examiner*—Zinna N. Davis
(74) *Attorney, Agent, or Firm*—Tina M. Tucker

(57) ABSTRACT

The present invention relates to a compound of Formula (I), which are useful for inhibiting resistant neoplasms where the resistance is conferred in part or in total by MRP1.

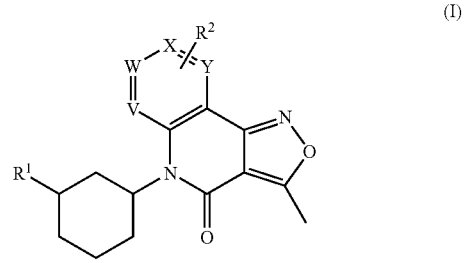

(I)

10 Claims, No Drawings

COMPOUNDS AND METHODS FOR INHIBITING MRP1

This is the national phase application, under 35 USC 371, for PCT/US02/06668, filed 28 Mar. 2002, which claims benefit, under 35 USC 119(e), of U.S. provisional application 60/282,641, filed 09 Apr. 2001.

Along with surgery and radiotherapy, chemotherapy continues to be an effective therapy for many cancers. In fact, several types of cancer, such as Hodgkin's disease, large cell lymphoma, acute lymphocytic leukemia, testicular cancer and early stage breast cancer, are now considered to be curable by chemotherapy. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", *Cancer Research*, 54:5902–5910, 1994. Doxorubicin, daunorubicin, epirubicin, vincristine, paclitaxel, mitoxantrone, melphalan, and etoposide are substrates of MRP1, i.e., MRP1 can bind to these oncolytics and redistribute them away from their site of action, the nucleus, and out of the cell. Id. and Marquardt, D., and Center, M. S., *Cancer Research*, 52:3157, 1992.

Doxorubicin, daunorubicin, and epirubicin are members of the anthracycline class of oncolytics. They are isolates of various strains of *Streptomyces* and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

PCT publications WO 99/07343, WO 99/51236, and WO 99/51228, disclose compounds which are known to be useful as MRP1 modulators. There remains a need to discover additional compounds that will modulate MRP1 in various diseases.

The present invention relates to a compound of formula I:

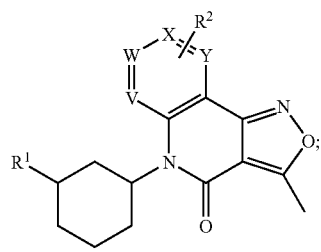

wherein:
any one of V, W, X, or Y is nitrogen;
$R^1$ is $NHR^3$, $CH_2NHR^3$, $CH_2C(O)NHR^4$, or $C(O)NHR^4$;
$R^2$ is hydrogen, halo, or trifluoromethyl;
$R^3$ is $C(O)OR^5$ or $C(O)R^6$;
$R^4$ is optionally substituted phenyl or $CH_2$-(optionally substituted phenyl);
$R^5$ is optionally substituted phenyl, optionally substituted heterocycle, or CH(OH)-(optionally substituted phenyl);
$R^6$ is optionally substituted phenyl, optionally substituted heterocycle, or CH(OH)-(optionally substituted phenyl); or a pharmaceutical salt thereof.

The present invention further relates to a method of inhibiting MRP1 in a mammal which comprises administering to a mammal in need thereof an effective amount of a compound of formula I, or a pharmaceutical salt thereof.

In another embodiment, the present invention relates to a method of inhibiting a resistant neoplasm, or a neoplasm susceptible to resistance in a mammal, which comprises administering to a mammal in need thereof an effective amount of a compound of formula I, or a pharmaceutical salt thereof, in combination with an effective amount of an oncolytic agent.

Furthermore, this invention provides the use of a compound of Formula I for the manufacture of a medicament for the inhibition of MRP1. This invention also provides the use of a compound of Formula I for the manufacture of a medicament for the inhibition of a resistant neoplasm.

The present invention also relates to a pharmaceutical formulation comprising a compound of formula I, or a pharmaceutical salt thereof, in combination with one or more oncolytics, pharmaceutical carriers, diluents, or excipients therefor.

The current invention concerns the discovery that a select group of compounds, those of formula I, are selective inhibitors of multidrug resistant protein (MRP1) and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic" refers to an amount of oncolytic capable of inhibiting a neoplasm, resistant or otherwise.

The term "inhibiting a resistant neoplasm or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm that is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm which is "susceptible to resistance" is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytics where at least one oncolytic is a substrate of MRP1. A "substrate of MRP1" is an oncolytic that binds to MRP1 and is redistributed away from the oncolytics site of action, (the neoplasm's nucleus) and out of the cell, thus, rendering the therapy less effective.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight, branched, or cyclic saturated hydrocarbon containing from 1 to 6 carbon atoms and includes $C_1$–$C_4$ alkyl groups. In addition, $C_1$–$C_6$ alkyl also includes, but is not limited to, cyclopentyl, pentyl, hexyl, cyclohexyl, and the like. The term "$C_3$–$C_6$ cycloalkyl" refers to cyclopropyl, cyclobutyl, cyclopentyl, and cyclohexyl. The term "$C_5$–$C_7$ cycloalkyl" refers to cyclopentyl, cyclohexyl, and cycloheptyl. The term "$C_6$–$C_{10}$ bicycloalkyl" refers to bicyclo-[2.1.1]hexanyl, [2.2.1]heptanyl, [3.2.1]octanyl, [2.2.2]octanyl, [3.2.2]nonanyl, [3.3.1]nonanyl, [3.3.2]decanyl, and [4.3.1]decanyl ring system where the ring is connected to the parent molecular moiety at any point available for substitution on the ring.

The terms "$C_1$–$C_4$ alkoxy" and "$C_1$–$C_6$ alkoxy" refer to moieties of the formula O—($C_1$–$C_4$ alkyl) and O—($C_1$–$C_6$ alkyl) respectively.

The term "halo" or "halide" refers to fluoro, chloro, bromo, and iodo.

The term "optionally substituted phenyl" refers to a phenyl ring optionally substituted 1 or 3 times independently with a $C_1$–$C_6$ alkyl, $C_1$–$C_4$ alkoxy, halo, benzyl, phenyl, or trifluoromethyl.

The term "heterocycle" refers to a monovalent, saturated, unsaturated, or aromatic mono cyclic or fused ring system of 5 to 7 total atoms respectively containing 1 to 3 heteroatoms selected independently from oxygen, sulfur, and nitrogen.

The term "optionally substituted heterocycle" refers to a heterocycle ring optionally substituted 1 or 2 times independently with a $C_1$–$C_6$ alkyl, $C_1$–$C_4$ alkoxy, halo, benzyl, phenyl, trifluoromethyl, or an oxo group.

The term "protecting group" (Pg) refers to an amino protecting group or a hydroxy protecting group. The species of protecting group will be evident from whether the "Pg" group is attached to a nitrogen atom (amino protecting group) or attached to an oxygen atom (hydroxy protecting group).

The term "amino protecting group" as used herein refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like. The species of amino protecting group employed is not critical so long as the derivatized amino group is stable to the condition of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, *Protective Groups in Organic Synthesis,* John Wiley and Sons, New York, N.Y., 1991, Chapter 7. This book shall be referred to hereafter as "*Greene*". A preferred amino protecting group is t-butyloxycarbonyl.

The term "hydroxy protecting group" denotes a group understood by one skilled in the organic chemical arts of the type described in Chapter 2 of *Greene*. Representative hydroxy protecting groups include, for example, ether groups including methyl and substituted methyl ether groups such as methyl ether, methoxymethyl ether, methylthiomethyl ether, tert-buylthiomethyl ether, (phenyldimethylsilyl) methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)-ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono-, di-, and trichloroacetate esters, phenoxyacetate ester, and p-chlorophenoxyacetate and the like. The species of hydroxy protecting group employed is not critical so long as the derivatized hydroxy group is stable to the conditions of subsequent reaction(s) on other positions of the intermediate molecule and can be selectively removed at the appropriate point without disrupting the remainder of the molecule including any other hydroxy protecting group(s).

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D.C., "Pharmaceutical Salts", *J. Pharm Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, 1,5-naphthalene-disulfonate, naphthalene-1-sulfonate, naphthalene-2-sulfonate, mandelate and the like.

The term "base addition salt" refers to a salt of a compound of formula I prepared by reaction of a compound of formula I with a mineral or organic base. For exemplification of pharmaceutical base addition salts see, e.g., Berge, S. M, Bighley, L. D., and Monkhouse, D. C., *J. Pharm. Sci.*, 66:1, 1977. This invention also contemplates pharmaceutical base addition salts of compounds of formula I. The skilled artisan would appreciate that some compounds of formula I may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of formula I.

While all of the compounds of the present invention are useful, certain of the compounds are particularly interesting and are preferred. The following listing sets out several groups of preferred compounds. It will be understood that each of the listings may be combined with other listings to create additional groups of preferred embodiments.

a) $R^1$ is $CH_2NHR^3$;
b) $R^2$ is hydrogen o trifluoromethyl;
c) $R^3$ is $C(O)R^6$;
d) $R^6$ is phenyl or optionally substituted heterocycle;
e) The compound is a pharmaceutical salt;
f) The compound is the hydrochloride salt;
g) The compounds of the Examples section;
h) The method where the mammal is a human;
i) The method where the oncolytic(s) is selected from doxorubicin, daunorubicin, epirubicin, vincristine, and etoposide;
j) The method where the neoplasm is of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, or bronchogenic carcinoma;
k) The formulation where the oncolytic(s) is selected from the group doxorubicin, daunorubicin, epirubicin, vincristine, and etoposide.

The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I may be prepared from compounds of formula II as illustrated in Scheme 1 below where V, W, X, Y, $R^1$ and $R^2$ are as described supra. $R^1$ may be a described supra or may be a protecting group.

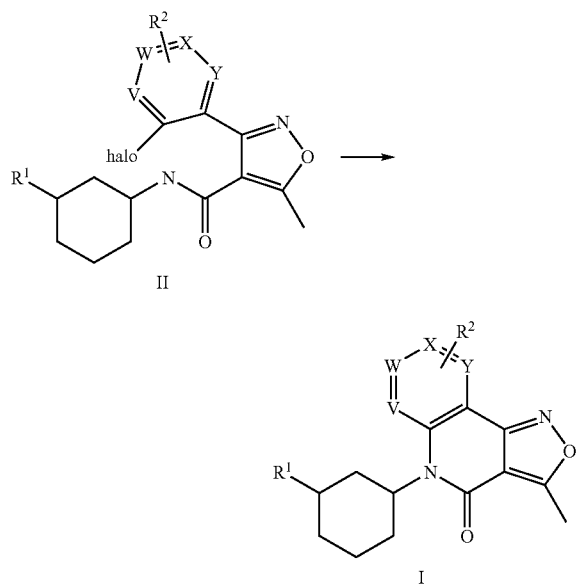

Scheme 1

Compounds of formula I may be prepared by dissolving or suspending a compound of formula II in a suitable solvent, preferably dimethylformamide, and adding a suitable base, including potassium methoxide, potassium tert-butoxide, potassium bis(trimethylsilyl)amide, potassium carbonate, sodium hexamethyldisilazane, and potassium hexamethyldisilazane. The base is typically employed in a one to one ratio. However, as the skilled artisan would appreciate, a slight molar excess, usually in about a 1.1 to about a 3 fold molar excess relative to the compound of formula II, is acceptable.

The reactants are typically combined at a temperature from about 0° C. to about 100° C. The reactants are preferably combined at room temperature, and the resulting solution is typically mixed for about 5 minutes to about 18 hours, preferably from about 15 minutes to about 1 hour.

Any protecting groups remaining in the cyclized compound of formula I may be removed as taught in *Greene* to provide additional compounds of formula I. Preferred choices of protecting groups and methods for their removal may be found in the Preparations and Examples sections below.

Where V, W, X, Y, R¹, and R² are as described supra, compounds of formula II may be prepared according to Scheme 2. R¹ may be a described supra or may be a protecting group.

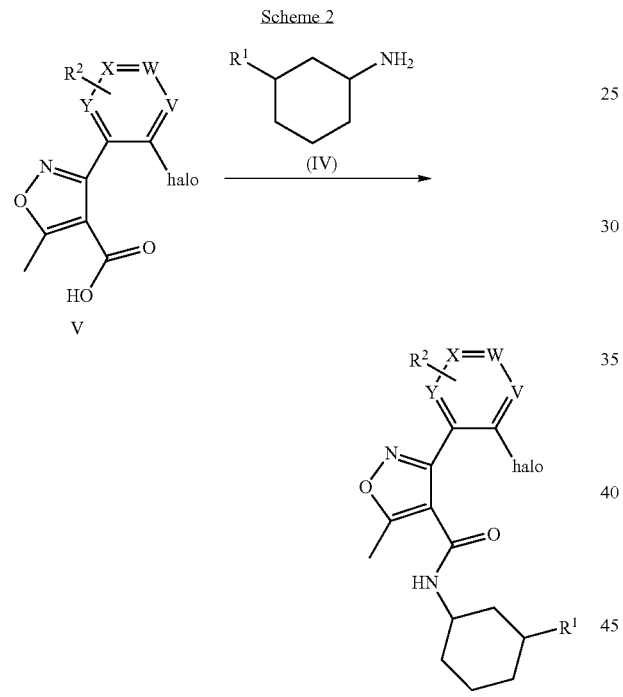

Compounds of formula V may be converted to the corresponding acid halide by methods well known to one skilled in the art. Compounds of formula II may be prepared by dissolving or suspending an acid halide of a compound of formula V in a suitable solvent and adding a compound of formula IV in a suitable solvent. Triethylamine, N,N-diisopropylethyl amine, dichloromethane, dimethylformamide, and mixtures thereof are convenient solvents. This amide forming reaction may also be run in the presence of 4-dimethylaminopyridine (DMAP), 1-(3-dimethyl-aminopropyl)-3-ethylcarbodiimide hydrochloride (EDCI), or 1-hydroxy-7-azabenzotriazole. The compound of formula V is preferably the corresponding carboxylic acid and is employed in an equimolar amount, relative to the compound of formula IV, but a slight excess (about a 0.05 to about 0.15 molar excess) is acceptable. DMAP is employed in a catalytic fashion. For example, about 5 molar percent to about 15 molar percent, relative to the compound of formula IV, is typically employed. A 10 molar percent is usually preferred.

Compounds of formula IV are well known in the art and to the extent not commercially available, are readily synthesized by standard procedures commonly employed in the art.

Compounds of formula V may be prepared in a manner similar to that described in Scheme 3.

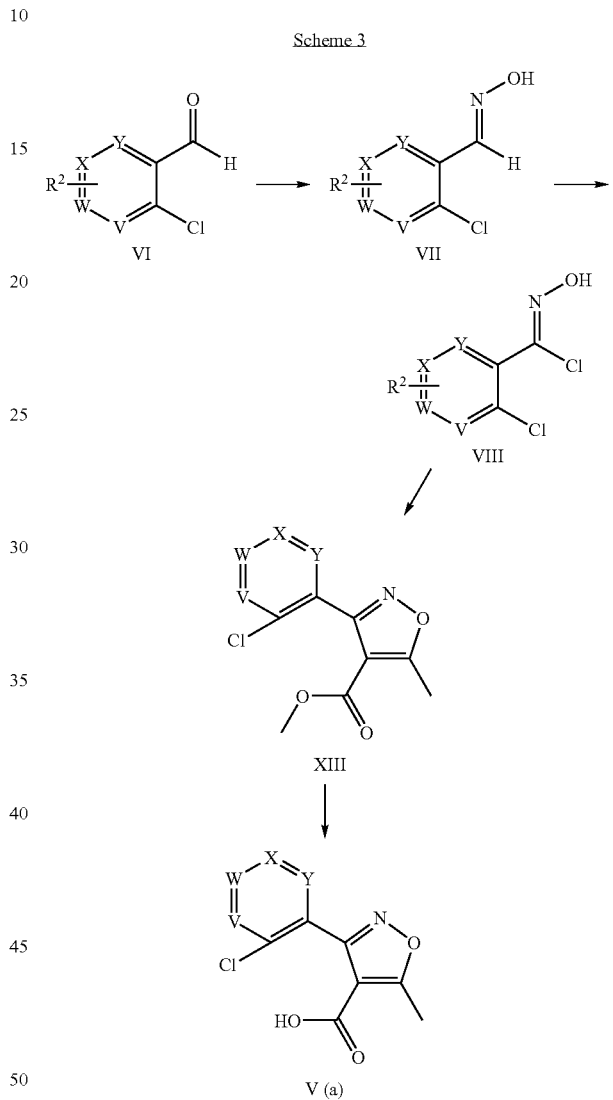

Compounds of formula VII may be prepared by dissolving or suspending a compound of formula VI in a suitable solvent with hydroxylamine hydrochloride and adding a suitable base, dropwise. Ethanol/water is a convenient solvent and is typically preferred. Sodium hydroxide is the preferred base. The compound of formula VI is typically and preferably employed in an equimolar amount, relative to the hydroxylamine, but a slight excess is acceptable. The reactants are preferably combined at about 0° C. and the resulting solution is typically warmed to room temperature and mixed for from about 1 to about 3 hours.

The compound of formula VII may then be converted to the compound of formula VIII by methods well known to the skilled artisan. For preferred methods, see preparations 3, 11, 20, and 28.

The compound of formula VIII may then be converted to the compound of formula XIII by dissolving or suspending a compound of formula VIII in a suitable solvent and adding methyl-2-butynoate and an appropriate base. Diethyl ether is a convenient solvent and is typically preferred. Triethylamine is a convenient base and is typically preferred. The ester group is then hydrolyzed to the corresponding carboxylic acid of formula V(a) through standard procedures commonly employed in the art, see for example, Larock, *Comprehensive Organic Transformations*, pgs. 981–985, VCH Publishers, New York, N.Y., 1999.

It should be recognized that the particular counterion forming a part of any salt of this invention is not of a critical nature, so long as the salt as a whole is pharmacologically acceptable and as long as the counterion does not contribute undesired qualities to the salt as a whole.

The optimal time for performing the reactions of Schemes 1–3 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and may then be collected by filtration, or the reaction solvent may be removed by extraction, evaporation, or decantation. The intermediates and final products of formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example "°C.", "N", "mmol", "g", "mL", "M", "HPLC", "IR", "MS(FD)", "MS(IS)", "MS(FIA)", "MS (FAB)", "MS(EI)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, ultraviolet spectrometry, and proton nuclear magnetic resonance spectrometry respectively. In addition, the absorption maxima listed for the IR spectra are only those of interest and not all of the maxima observed.

Preparations

Preparation 1

2-Chloropyridine-3-carboxaldehyde

Form a solution of lithium diisopropylamide by the adding n-butyl lithium (37.5 mL, 0.06 mol, 1.6 M in hexanes) to diisopropylamine (8.39 mL, 0.06 mol) in tetrahydrofuran (200 mL) at −10 to −20° C. under a nitrogen atmosphere. After stirring for 20 min., cool the mixture to −70° C. and add 2-chloropyridine (4.96 mL, 0.05 mol) dropwise via syringe and stir the mixture for 1 hour at this temperature. Add N,N-dimethylformamide (7.73 mL, 0.10 mol) dropwise via syringe and stir for 1 hour near −70° C. after which time remove the cooling bath and add a solution of aqueous 5N hydrochloric acid/tetrahydrofuran (5 ml125 mL) in a dropwise manner. Add water (200 mL) and warm the mixture to −10° C. Extract with ethyl acetate. Dry the combined extracts over sodium sulfate and concentrate in vacuo. Elute the resulting residue over silica gel using 10% ethyl acetate/ hexanes allowing for isolation of the desired aldehyde (2.86 g, 40%) as a solid. MS(EI): (M)$^+$ 140.2, 141.3, 143.3 m/z.

Preparation 2

2-Chloropyridine-3-carboxaldehyde oxime

Combine 2-chloropyridine-3-carboxaldehyde (2.75 g, 0.0195 mol) with hydroxylamine hydrochloride (1.38 g, 0.021 mol) and ice (40 g) in an ethanol/water (15 mL/15 mL) mixture. Add aqueous sodium hydroxide (1.95 g, 0.049 mol, in 5 mL of water) dropwise and stir for 2.5 h near ambient temperature. Adjust the mixture to approx. pH 7.0 with aqueous hydrochloric acid, allowing for product precipitation. Extract with diethyl ether and wash with water and dry over sodium sulfate. Concentrate to obtain the desired crude oxime (2.78 g, 91%) as a white solid. MS(EI): (M)$^+$ 156.3, 158.3 m/z.

Preparation 3

Chloro(2-chloro(3-pyridyl))(hydroxyimino)methane

Dissolve 2-chloropyridine-3-carboxaldehyde oxime (2.50 g, 0.016 mol) in N,N-dimethylformamide (20 mL). Add N-chlorosuccinimide (2.14 g, 0.016 mol) in small portions along with a small amount of gaseous hydrochloric acid. Stir for 3 hours. When TLC analysis indicates the reaction to be complete, pour into ice/water. Extract with diethyl ether and wash the combined extracts with water and dry over sodium sulfate. Concentrate the extracts to give 3.00 g (98%) of crude product as an off white solid. MS(FD): (M)$^+$ 190.0, 192.0 m/z.

Preparation 4

3-(2-Chloro-pyridin-3-yl)-5-methyl-isoxazole-4-carboxylic acid methyl ester

Combine chloro(2-chloro(3-pyridyl))(hydroxyimino) methane (2.90 g, 0.015 mol) with methyl-2-butynoate (1.19 mL, 0.012 mol) in diethyl ether (75 mL). Cool the mixture in an ice bath under a nitrogen atmosphere. Add a solution of triethylamine (1.77 mL, 0.013 mol) in diethyl ether (10 mL) in a dropwise manner. Stir the mixture overnight while warming to ambient temperature. Quench the mixture with water and extract with diethyl ether. Concentrate the combined extracts and elute over silica gel with 10% methanol/ dichloromethane to give the desired isoxazole along with a co-eluting impurity (2.30 g, 60%). MS(ES): (M+1)$^+$ 253.0, 255.0 m/z.

Preparation 5

3-(2-Chloro-pyridin-3-yl)-5-methyl-isoxazole-4-carboxylic acid

Combine 3-(2-chloro-pyridin-3-yl)-5-methyl-isoxazole-4-carboxylic acid methyl ester (1.90 g, 0.0075 mol) with aqueous sodium hydroxide (2N, 15.0 mL, 0.03 mol), ethanol (3 mL), and tetrahydrofuran (3 mL). Stir for 4 hours at ambient temperature. Remove the organic solvents in vacuo and adjust the aqueous mixture to approx. pH 3.0 with aqueous hydrochloric acid. Extract with ethyl acetate and dry the combined extracts over sodium sulfate and concentrate in vacuo. Eluted over silica gel with methanol/dichloromethane allowing for isolation of the desired isoxazole acid as an off white solid (0.98 g, 55%). MS(ES): $(M+1)^+$ 238.97, 240.97 m/z.

Preparation 6

(3-{[3-(2-Chloro-pyridin-3-yl)-5-methyl-isoxazole-4-carbonyl]-amino}-cyclohexylmethyl)-carbamic acid benzyl ester Combine 3-(2-chloro-pyridin-3-yl)-5-methyl-isoxazole-4-carboxylic acid (0.50 g, 0.0021 mol) with (3-amino-cyclohexylmethyl)-carbamic acid benzyl ester (0.63 g, 0.0021 mol), 1-[3-(dimethyl-amino)propyl]-3-ethylcarbodiimide hydrochloride (0.40, 0.0021 mol), 1-hydroxy-7-azabenzo-triazole (0.29 g, 0.0021 mol), and N,N-diisopropyl-ethyl amine (1.10 mL, 0.0063 mol), in N,N-dimethylformamide (10 mL). Stir over a weekend at ambient temperature. Concentrate in vacuo and take up in water and extract with ethyl acetate. Wash the combined extracts with water, dry over sodium sulfate, and concentrate in vacuo. Elute over silica gel using ethanol/dichloromethane allowing for the isolation of 0.87 g (86%) of the desired amide as a white solid. MS(ES): $(M+1)^+$ 483.1, 485.1 m/z.

Preparation 7

[3-(3-Methyl-4-oxo-5H-2-oxa-1,5,6-triaza-cyclopenta-[a]naphthalen-5-yl)-cyclohexylmethyl]-carbamic acid benzyl ester Dissolve (3-{[3-(2-chloro-pyridin-3-yl)-5-methyl-isoxazole-4-carbonyl]-amino}-cyclohexylmethyl)-carbamic acid benzyl ester (0.74 g, 0.0015 mol) in N,N-dimethylformamide (10 mL) at ambient temperature under a nitrogen atmosphere. Add a solution of potassium bis(trimethylsilyl) amide (0.5 M in toluene, 3.38 mL, 0.0017 mol) and stir for 15 min. at ambient temperature. Quench the dark mixture with water and follow by the addition of solid sodium chloride. Extract with ethyl acetate and wash the combined extracts with water and dry over sodium sulfate. Concentrate and elute over silica gel with methanol/dichloromethane to give the isolation of 0.61 g (89%) of the desired product as a white fluffy solid. MS(ES): $(M+1)^+$ 447.1, 448.1 m/z.

Preparation 8

5-(3-Aminomethyl-cyclohexyl)-3-methyl-5H-2-oxa-1,5,6-triaza-cyclopenta[a]naphthalen-4-one hydroiodide Dissolve [3-(3-methyl-4-oxo-5H-2-oxa-1,5,6-triaza-cyclopenta-[a]naphthalen-5yl)-cyclohexylmethyl]-carbamic acid benzyl ester (0.52 g, 0.0012 mol) in dry dichloromethane and cool in an ice bath under nitrogen. Add iodotrimethylsilane (0.50 mL, 0.0035 mol) and stir overnight while warming to ambient temperature. Quench the mixture with methanol (approx. 5 mL) and concentrate in vacuo. Take up the resulting residue in minimal dichloromethane and add diethyl ether. Concentrate and titrate from dichloromethane/diethyl ether to give a dark solid. Decant the solvent and dry the solid in vacuo to give a near quantitative yield of the crude amine salt as a dark solid. Use directly without purification. MS(ES): $(M+1)^+$ 313.2, 314.2 m/z.

Preparation 9

3-Fluoropyridine-4-carboxaldehyde

Form a solution of lithium diisopropylamide by the addition of n-butyl lithium (37.5 mL, 0.06 mol, 1.6 M in hexanes) to diisopropylamine (8.40 mL, 0.06 mol) in tetrahydrofuran (200 mL) at 0 to −10° C. under a nitrogen atmosphere. Stir for 30 min. Cool to −70° C. and add 3-fluoropyridine (4.29 mL, 0.05 mol) dropwise via syringe. Stir for 1 hour at this temperature. Add N,N-dimethylformamide (7.75 mL, 0.10 mol) dropwise via syringe and stir for 2 hours near −70° C. Add water (200 mL) when the mixture warms to −20° C. and extract with ethyl acetate. Dry the combined extracts over sodium sulfate and concentrate in vacuo. Elute the resulting residue over silica gel, allowing for isolation of the desired aldehyde (4.28 g, 68%) as an oil. MSEI): $M^+$ 125.0 m/z.

Preparation 10

3-Fluoropyridine-4-carboxaldehyde oxime

Combine 3-fluoropyridine-4-carboxaldehyde (2.37 g, 0.037 mol) and ice (50 g) in an ethanol/water (30 mL/30 mL) mixture. Add aqueous sodium hydroxide (3.41 g, 0.083 mol, in 30 mL of water) dropwise and stir for 3 h near ambient temperature. Adjust the mixture to approx. pH 7.0 with aqueous hydrochloric acid and extract with diethyl ether. Dry the combined extracts over sodium sulfate and concentrate in vacuo which leaves the desired crude oxime (4.60 g, 98%) as a white solid. MS(FS): $(M+1)^+$ 141.0, 142.0 m/z.

Preparation 11

Chloro(2-fluoro(3-pyridyl))(hydroxyimino)methane

Dissolve 3-fluoropyridine-4-carboxaldehyde oxime (4.60 g, 0.033 mol) in N,N-dimethylformamide (30 mL). Add N-chlorosuccinimide (4.97 g, 0.037 mol) in small portions and stir over a weekend at ambient temperature. Pour the mixture into ice/water and extract with diethyl ether. Dry the combined extracts over sodium sulfate and concentrate in vacuo which results in the recovery of near quantitative amount of crude product as a tan solid. MS(FD): $M^+$ 174.0, 176.0 m/z.

Preparation 12

3-(3-Fluoro-pyridin-4-yl)-5-methyl-isoxazole-4-carboxylic acid ethyl ester

Combine chloro(2-fluoro(3-pyridyl))(hydroxyimino)methane (5.70 g, 0.033 mol) with ethyl-2-butynoate (9.70 mL, 0.083 mol) in diethyl ether (150 mL) and cool in an ice bath under a nitrogen atmosphere. Add triethylamine (6.03 mL, 0.043 mol) dropwise and stir overnight while warming to ambient temperature. Quench the mixture with water and extract with ethyl acetate. Concentrate the combined extracts and elute over silica gel with methanol/dichloromethane resulting in recovery of the desired isoxazole (2.15 g, 26%) as an oil which solidified upon standing. ES(EI): M+ 250.1, 251.1 m/z.

Preparation 13

3-(3-Fluoro-pyridin-4-yl)-5-methyl-isoxazole-4-carboxylic acid

Combine 3-(3-fluoro-pyridin-4-yl)-5-methyl-isoxazole-4-carboxylic acid ethyl ester (2.00 g, 0.008 mol) with aqueous sodium hydroxide (2N, 15.0 mL, 0.03 mol), ethanol (3 mL), and tetrahydrofuran (3 mL) and stir overnight at ambient temperature. Remove the organic solvents in vacuo and adjust the aqueous mixture to approx. pH 3.5 with aqueous hydrochloric acid. Extract with ethyl acetate and dry the combined extracts over sodium sulfate and concentrate in vacuo. Drying nets the desired isoxazole acid as an off white solid (1.35 g, 76%). MS(FD): M+ 223.2 m/z.

Preparation 14

(3-{[3-(3-Fluoro-pyridin-4-yl)-5-methyl-isoxazole-4-carbonyl]-amino}-cyclohexylmethyl)-carbamic acid benzyl ester Combine 3-(3-fluoro-pyridin-4-yl)-5-methyl-isoxazole-4-carboxylic acid (0.41 g, 0.0019 mol) with (3-amino-cyclohexylmethyl)-carbamic acid benzyl ester (0.55 g, 0.0019 mol), 1-[3-(dimethylamino)propyl]-3-ethylcarbodiimide hydrochloride (0.36, 0.0019 mol), 1-hydroxy-7-azabenzo-triazole (0.25 g, 0.0019 mol), and N,N-diisopropyl-ethyl amine (0.96 mL, 0.0055 mol), in N,N-dimethylformamide (10 mL). Stir the mixture overnight at ambient temperature. Concentrate in vacuo and take up the residue in water and extract with ethyl acetate. Concentrate and elute over silica gel using methanol/dichloromethane resulting in the isolation of 0.66 g (76%) of the desired amide as a light yellowish solid. MS(ES): (M+1)+ 467.0, 468.1 m/z.

Preparation 15

[3-(3-Methyl-4-oxo-5H-2-oxa-1,5,7-triaza-cyclopenta[a]naphthalen-5-yl)-cyclohexylmethyl]-carbamic acid benzyl ester Dissolve (3-{[3-(3-fluoro-pyridin-4-yl)-5-methyl-isoxazole-4-carbonyl]-amino}-cyclohexylmethyl)-carbamic acid benzyl ester (0.65 g, 0.0014 mol) in N,N-dimethylformamide (6 mL) at ambient temperature under a nitrogen atmosphere. Add a solution of potassium bis(trimethylsilyl) amide (0.5 M in toluene, 3.35 mL, 0.0017 mol) and stir for 15 min. at ambient temperature. Quench the dark mixture with water and follow with the addition of solid sodium chloride. Extract with ethyl acetate and wash the combined extracts with water and dry over sodium sulfate. Concentrate and elute over silica gel with methanol/dichloromethane allowing for the isolation of 0.44 g (71%) of the desired product as an off white solid. MS(S): (M+1)+ 447.2, 448.2 m/z.

Preparation 16

5-(3-Aminomethyl-cyclohexyl)-3-methyl-5H-2-oxa-1,5,7-triaza-cyclopenta[a]naphthalen-4-one hydroiodide Dissolve [3-(3-methyl-4-oxo-5H-2-oxa-1,5,7-triaza-cyclopenta[a]naphthalen-5-yl)-cyclohexylmethyl]-carbamic acid benzyl ester (0.42 g, 0.00093 mol) in dry dichloromethane. Add iodotrimethylsilane (0.33 mL, 0.0023 mol) and stir overnight at ambient temperature. Quench the mixture with methanol (5 mL) and concentrate in vacuo. Take up the resulting residue in minimal dichloromethane and add diethyl ether. Concentrate and titrate from dichloromethane/diethyl ether to form a dark solid. Decant the solvent and the dry in vacuo to give a near quantitative amount of the crude amine salt as a dark solid and used directly without purification. MS(ES): (M+1)+ 313.2, 314.2 m/z.

Preparation 17

4-Chloropyridine-3-carboxaldehyde

Form a solution of lithium diisopropylamide by the adding n-butyl lithium (37.5 mL, 0.06 mol, 1.6 M in hexanes) to diisopropylamine (8.40 mL, 0.06 mol) in tetrahydrofuran (200 mL) at −10 to −20° C. under a nitrogen atmosphere. Stir for 30 min., and cool to −60° C. Add 4-chloropyridine hydrochloride (3.75 g, 0.025 mol) in small portions and stir for 1.5 hours at this temperature. Add dimethylformamide (4.0 mL, 0.052 mol) dropwise via syringe and stir for 1 hour near −60° C. Add water (200 mL) when the mixture has warmed near 0° C. Extract with ethyl acetate. Dry the combined extracts over sodium sulfate and concentrate in vacuo. Elute the resulting residue over silica with methanol/dichloromethane, allowing for isolation of the desired aldehyde (2.80 g, 79%) as a light yellowish solid. MS(BI): (M)+ 141.0, 142.0, 143.0 m/z.

Preparation 18

4-Chloropyridine-3-carboxaldehyde oxime

Combine 4-chloropyridine-3-carboxaldehyde (2.75 g, 0.020 mol) with hydroxylamine hydrochloride (1.38 g, 0.021 mol) and ice (50 g) in an ethanol/water (25 mL/25 mL) mixture. Add aqueous sodium hydroxide (2.00 g, 0.049 mol, in 25 mL of water) dropwise and stir for 3 h near ambient temperature. Adjust the mixture to approx. pH 7.0 with aqueous hydrochloric acid and extract with diethyl ether. Dry the combined extracts over sodium sulfate and concentrate in vacuo which leaves the desired crude oxime (2.67 g, 88%). MS(ES): (M+1)+ 156.0, 158.0 m/z.

Preparation 19

Chloro(4-chloro(3-pyridyl))(hydroxyimino)methane

Dissolve 4-chloropyridine-3-carboxaldehyde oxime (2.60 g, 0.017 mol) in N,N-dimethylformamide (20 mL). Add N-chlorosuccinimide (2.48 g, 0.018 mol) in small portions and stir overnight at ambient temperature. Pour the mixture into water and extract with ethyl acetate. Wash the combined extracts with water and dry over sodium sulfate. Concentrate in vacuo to give 2.45 g (75%) of crude product as a yellowish solid. $^1$H NMR was consistent with structure.

Preparation 20

3-(4-Chloro-pyridin-3-yl)-5-methyl-isoxazole-4-carboxylic acid ethyl ester

Combine chloro(4-chloro(3-pyridyl))(hydroxyimino)methane (2.40 g, 0.013 mol) with ethyl-2-butynoate (3.66 mL, 0.031 mol) in diethyl ether (150 mL) under a nitrogen atmosphere. Add triethylamine (2.27 mL, 0.016 mol) in a dropwise manner and stir over a weekend at ambient temperature. Quench the mixture with water and extract with ethyl acetate. Concentrate the combined extracts and elute over silica gel with methanol/dichloromethane to give the desired isoxazole (0.95 g, 27%) as an oil. ES(EI): $M^+$ 266.0, 267.0, 268.0 m/z.

Preparation 21

3-(4-Chloro-pyridin-3-yl)-5-methyl-isoxazole-4-carboxylic acid

Combine 3-(4-chloro-pyridin-3-yl)-5-methyl-isoxazole-4-carboxylic acid ethyl ester (0.90 g, 0.003 mol) with aqueous sodium hydroxide (2N, 7.0 mL, 0.014 mol), ethanol (2 mL), and tetrahydrofuran (2 mL) and stir overnight at ambient temperature. Adjust the aqueous mixture to approx. pH 2.5 with aqueous hydrochloric acid. Extract with ethyl acetate and dry the combined extracts over sodium sulfate and concentrate in vacuo. Drying nets the desired isoxazole acid as a light solid (0.78 g, 97%). MS(ES): $(M+1)^+$ 239.0, 241.0 m/z.

Preparation 22

(3-{[3-(4-Chloro-pyridin-3-yl)-5-methyl-isoxazole-4-carbonyl]-amino}-cyclohexylmethyl)-carbamic acid benzyl ester Combine 3-(4-chloro-pyridin-3-yl)-5-methyl-isoxazole-4-carboxylic acid (0.50 g, 0.0021 mol) with (3-aminocyclohexylmethyl)-carbamic acid benzyl ester (0.63 g, 0.0021 mol), 1-[3-(dimethylamino)propyl]-3-ethylcarbodiimide hydrochloride (0.40, 0.0021 mol), 1-hydroxy-7-azabenzo-triazole (0.29 g, 0.0021 mol), and N,N-diisopropylethyl amine (1.10 mL, 0.0063 mol), in N,N-dimethylformamide (10 mL) and stir overnight at ambient temperature. Concentrate in vacuo and take up in water and extract with ethyl acetate. Wash the combined extracts with water and dry over sodium sulfate. Concentrate and elute over silica gel using methanol/dichloromethane to give 0.67 g (66%) of the desired amide. MS(ES): $(M+1)^+$ 483.2, 485.2 m/z.

Preparation 23

[3-(3-Methyl-4-oxo-5H-2-oxa-1,5,8-triaza-cyclopenta[a]naphthalen-5-yl)-cyclohexylmethyl]-carbamic acid benzyl ester Dissolve (3-{[3-(4-chloro-pyridin-3-yl)-5-methyl-isoxazole-4-carbonyl]-amino}-cyclohexylmethyl)-carbamic acid benzyl ester (0.63 g, 0.0013 mol) in N,N-dimethylformamide (10 mL) at ambient temperature under a nitrogen atmosphere. Add a solution of potassium bis(trimethylsilyl)amide (0.5 M in toluene, 3.12 mL, 0.0016 mol) and stir for 15 min. at ambient temperature. Quench the dark mixture with water and follow by the addition of solid sodium chloride. Extract with ethyl acetate and wash the combined extracts with water and dry over sodium sulfate. Concentrate and elute over silica gel with methanol/dichloromethane to give 0.47 g (81%) of the desired product as a white solid. MS(ES): $(M+1)^+$ 447.2, 448.2 m/z.

Preparation 24

5-(3-Aminomethyl-cyclohexyl)-3-methyl-5H-2-oxa-1,5,8-triaza-cyclopenta[a]naphthalen-4-one hydroiodide Dissolve [3-(3-methyl-4-oxo-5H-2-oxa-1,5,8-triaza-cyclopenta[a]naphthalen-5-yl)-cyclohexylmethyl]-carbamic acid benzyl ester (0.45 g, 0.0010 mol) in dry dichloromethane (10 mL). add iodotrimethylsilane (0.36 mL, 0.0025 mol) and stir overnight at ambient temperature. Quench the mixture with methanol (5 mL) and concentrate in vacuo. Take up in minimal dichloromethane and add diethyl ether. Concentrate and titrate from dichloromethane/diethyl ether to form a dark solid. Decant he solvent and dry the solid in vacuo to give a near quantitative amount of the crude amine salt as a dark solid and is used directly without purification. MS(ES): $(M+1)^+$ 313.2, 314.2 m/z.

Preparation 25

3,5-Dichloropyridine-4-carboxaldehyde

Form a solution of lithium diisopropylamide by the adding n-butyl lithium (37.5 mL, 0.06 mol, 1.6 M in hexanes) to diisopropylamine (8.40 mL, 0.06 mol) in tetrahydrofuran (200 mL) at −10 to−20° C. under a nitrogen atmosphere. Stir for 30 min., and cool to −60° C. Add 3,5-dichloropyridine hydrochloride (7.40 g, 0.05 mol) in small portions and stir for 1.5 hours at this temperature. Add N,N-dimethylformamide (7.75 mL, 0.10 mol) dropwise via syringe and stir for 1 hour near −60° C. Add water (200 mL) when the mixture is warmed near 0° C. and extract with ethyl acetate. Dry over sodium sulfate and concentrate in vacuo. Elute over silica gel with methanol/dichloromethane to give the desired aldehyde (2.94 g, 33%) as a light solid. MS(EI): Exact Mass Calc'd for: $C_6H_3NOCl_2$ 176.9562 m/z. Found: 176.9582 m/z.

Preparation 26

3,5-Dichloropyridine-4-carboxaldehyde oxime

Combine 3,5-dichloropyridine-4-carboxaldehyde (2.80 g, 0.016 mol) with hydroxylamine hydrochloride (1.13 g, 0.018 mol) and ice (50 g) in an ethanol/water (30 mL/30 mL) mixture. Add aqueous sodium hydroxide (1.63 g, 0.024 mol, in 20 mL of water) dropwise and stir for 4 h near ambient temperature. Adjust the mixture to approx. pH 7.0 with aqueous hydrochloric acid and extracte with diethyl ether. Dry the combined extracts over sodium sulfate and concentrate in vacuo to give the desired crude oxime (3.00 g, 88%) as a light solid. MS(ES): $(M+1)^+$ 190.9, 192.9 m/z.

Preparation 27

Chloro(2,5-dichloro(4-pyridyl))(hydroxyimino)methane

Dissolve 3,5-dichloropyridine-4-carboxaldehyde oxime (2.90 g, 0.015 mol) in N,N-dimethylformamide (20 mL).

Add N-chlorosuccinimide (2.26 g, 0.017 mol) in small portions and stir for 2 h at ambient temperature. Pour into water and extracte with ethyl acetate. Wash the combined extracts with water and dry over sodium sulfate. Concentrate in vacuo to give a near quantitative amount of a semi-solid and used without further purification. MS(ES): (M+1)$^+$ 205.95, 207.95 m/z.

Preparation 28

3-(3,5-Dichloro-pyridin-4-yl)-5-methyl-isoxazole-4-carboxylic acid ethyl ester

Combine chloro(2,5-dichloro(4-pyridyl))(hydroxyimino)methane (3.40 g, 0.015 mol) with ethyl-2-butynoate (5.11 g, 0.046 mol) in diethyl ether (150 mL) under a nitrogen atmosphere. Add triethylamine (2.75 mL, 0.020 mol) in a dropwise manner and stirirred overnight at ambient temperature. Quench the mixture with aqueous sodium bicarbonate and extracte with ethyl acetate. Concentrate and elute over silica gel with 20% ethyl acetate/hexanes to give the desired isoxazole (2.91 g, 64%) as an oil. ES(ES): (M+1)$^+$ 266.0, 301.0, 303.0 m/z.

Preparation 29

3-(3,5-Dichloro-pyridin-4-yl)-5-methyl-isoxazole-4-carboxylic acid

Combine 3-(3,5-dichloro-pyridin-4-yl)-5-methyl-isoxazole-4-carboxylic acid ethyl ester (2.75 g, 0.009 mol) with aqueous sodium hydroxide (2N, 30.0 mL, 0.06 mol), ethanol (5 mL), and tetrahydrofuran (5 mL) and stir overnight at ambient temperature. Remove the organic solvents in vacuo and adjust the aqueous mixture to approx. pH 2.0 with aqueous hydrochloric acid. Extract with ethyl acetate and dry the combined extracts over sodium sulfate and concentrate in vacuo. Drying nets the desired isoxazole acid as a light solid (2.42 g, 97%). MS(ES): (M+1)$^+$ 273.0, 275.0 m/z.

Preparation 30

(3-{[3-(3,5-Dichloro-pyridin-4-yl)-5-methyl-isoxazole-4-carbonyl]-amino}cyclohexylmethyl)-carbamic acid benzyl ester Combine 3-(3,5-dichloro-pyridin-4-yl)-5-methyl-isoxazole-4-carboxylic acid (0.41 g, 0.0015 mol) with (3-aminocyclohexylmethyl)-carbamic acid benzyl ester (0.45 g, 0.0015 mol), 1-[3-(dimethylamino)propyl]-3-ethylcarbodiimide hydrochloride (0.29, 0.0015 mol), 1-hydroxy-7-azabenzo-triazole (0.20 g, 0.0015 mol), and N,N-diisopropyl-ethyl amine (0.78 mL, 0.0045 mol), in N,N-dimethylformamide (10 mL) and stir over a weekend at ambient temperature. Concentrate the mixture in vacuo and take up in water and extracte with ethyl acetate. Dry over sodium sulfate. Concentrate and elute over silica gel using methanol/dichloromethane to give 0.64 g (82%) of the desired amide as a white foam. MS(ES): (M+1)$^+$ 516.9, 518.9 m/z.

Preparation 31

[3-(9-Chloro-3-methyl-4-oxo-5H-2-oxa-1,5,7-triaza-cyclopenta[a]naphthalen-5-yl)cyclohexylmethyl]-carbamic acid benzyl ester Dissolve (3-{[3-(3,5-dichloro-pyridin-4-yl)-5-methyl-isoxazole-4-carbonyl]amino}-cyclohexylmethyl)-carbamic acid benzyl ester (0.60 g, 0.0012 mol) in N,N-dimethylformamide (5 mL) at ambient temperature under a nitrogen atmosphere. Add a solution of potassium bis(trimethylsilyl)amide (0.5 M in toluene, 2.32 mL, 0.0012 mol) and stir for 20 min. at ambient temperature. Quench the dark mixture with water and follow by the adding solid sodium chloride. Extract with ethyl acetate and dry over sodium sulfate. Concentrate and elute over silica gel with methanol/dichloromethane to give 0.33 g (58%) of the desired product. MS(ES): (M+1)$^+$ 481.0 m/z.

Preparation 32

3-Fluoropyridine-2-carboxaldehyde

Add a solution of n-butyl lithium (34.4 mL, 0.055 mol, 1.6 M in hexanes) to a mixture of 1,4-diazabicyclo-[2.2.2]octane (6.16, 0.055 mol) in diethyl ether (250 mL) at −10 to−20° C. under a nitrogen atmosphere. Stir for 1 h and cool to −70° C. Add 3-fluoropyridine (4.29 mL, 0.05 mol) dropwise and stir for 2.5 hours at this temperature. Add N,N-dimethylformamide (7.75 mL, 0.10 mol) dropwise via syringe and stir for 1 hour near −70° C. Add water (200 mL) when the mixture warms near −20° C. and extract with ethyl acetate. Dry over sodium sulfate and concentrate in vacuo. Elute over silica gel with dichloromethane to give the desired aldehyde (3.06 g, 49%) as a dark solid. MS(ES): (M+1)$^+$ 126.0 m/z.

Preparation 33

3-Fluoropyridine-2-carboxaldehyde oxime

Combine 3-fluoropyridine-2-carboxaldehyde (3.00 g, 0.024 mol) with hydroxylamine hydrochloride (1.70 g, 0.026 mol) and ice (50 g) in an ethanol/water (30 mL/30 mL) mixture. Add aqueous sodium hydroxide (2.46 g, 0.06 mol, in 25 mL of water) dropwise and stir for 4 h near ambient temperature. Adjust the mixture to approx. pH 7.0 with aqueous hydrochloric acid and extract with diethyl ether. Dry over sodium sulfate and concentrate in vacuo. Elute the resulting residue over silica gel using methanol/dichloromethane to give 2.59 g (77%) of the desired oxime as an off white solid. MS(ES): (M+1)$^+$ 140.9, 142.0 m/z.

Preparation 34

3-(3-Fluoro-pyridin-2-yl)-5-methyl-isoxazole-4-carboxylic acid ethyl ester

Dissolve 3-fluoropyridine-2-carboxaldehyde oxime (2.55 g, 0.018 mol) in N,N-dimethylformamide (20 mL). Add N-chlorosuccinimide (2.71 g, 0.02 mol) in small portions and stir for 6 h at ambient temperature. Pour into water and extracte with ethyl acetate. Wash the combined extracts with water and dry over sodium sulfate. Concentrate in vacuo to give crude product. Use without further purification. MS(FD): M$^+$ 174.0, 175.9 m/z. Combine this material with ethyl-2-butynoate (5.30 mL, 0.046 mol) in diethyl ether (200 mL) under a nitrogen atmosphere. Add triethylamine (3.29 mL, 0.024 mol) in a dropwise manner and stir over a weekend at ambient temperature. Quench the mixture with water and extract with ethyl acetate. Dry the combined extracts over sodium sulfate and concentrate. Elute over silica gel with methanol/dichloromethane to give the desired isoxazole (0.52 g, 11%). ES(ES): (M+1)$^+$ 251.0, 252.0 m/z.

Preparation 35

3-(3-Fluoro-pyridin-2-yl)-5-methyl-isoxazole-4-carboxylic acid

Combine 3-(3-fluoro-pyridin-2-yl)-5-methyl-isoxazole-4-carboxylic acid ethyl ester (0.515 g, 0.002 mol) with aqueous sodium hydroxide (2N, 8.0 mL, 0.016 mol), ethanol (2 mL), and tetrahydrofuran (2 mL) and stir overnight at ambient temperature. Add water and adjust to approx. pH 2.0 with aqueous hydrochloric acid. Extract with ethyl acetate and dry over sodium sulfate and concentrate in vacuo. Drying nets the desired isoxazole acid (0.44 g, 97%). MS(ES): $(M+1)^+$ 221.9, 222.9 m/z.

Preparation 36

3-({[3-Fluoro-pyridin-2-yl)-5-methyl-isoxazole-4-carbonyl]-amino}-cyclohexylmethyl)-carbamic acid benzyl ester Combine 3-(3-fluoro-pyridin-2-yl)-5-methyl-isoxazole-4-carboxylic acid (0.425 g, 0.0019 mol) with (3-amino-cyclohexylmethyl)-carbamic acid benzyl ester (0.57 g, 0.0019 mol), 1-[3-(dimethylamino)propyl]-3-ethylcarbodiimide hydrochloride (0.37, 0.0019 mol), 1-hydroxy-7-azabenzo-triazole (0.26 g, 0.0019 mol), and N,N-diisopropylethyl amine (1.0 mL, 0.0057 mol), in N,N-dimethylformamide (8 mL) and stir overnight at ambient temperature. Concentrate in vacuo and take up in water and extract with ethyl acetate. Dry the combined extracts over sodium sulfate. Concentrate and elute over silica gel using methanol/dichloromethane to give 0.265 g (30%) of the desired amide. MS(ES): $(M+1)^+$ 467.2, 468.2 m/z.

Preparation 37

[3-(3-Methyl-4-oxo-5H-2-oxa-1,5,9-triaza-cyclopenta[a]naphthalen-5-yl)-cyclohexylmethyl]-carbamic acid benzyl ester Dissolve (3-{[3-(3-fluoro-pyridin-2-yl)-5-methyl-isoxazole-4-carbonyl]-amino}-cyclohexylmethyl)-carbamic acid benzyl ester (260 mg, 0.56 mmol) in N,N-dimethylformamide (5 mL) at ambient temperature under a nitrogen atmosphere. Add a solution of potassium bis(trimethylsilyl) amide (0.5 M in toluene, 1.34 mL, 0.67 mmol) and stir for 15 min. at ambient temperature. Quench the dark mixture with water and follow by the adding solid sodium chloride. Extract with ethyl acetate and wash with water and dry over sodium sulfate. Concentrate and elute over silica gel with methanol/dichloromethane to give 131 mg (53%) of the desired product. MS(ES): $(M+1)^+$ 447.2, 448.2 m/z.

Preparation 38

3-(3-chloro-5-trifluoromethyl-pyririn-2-yl)-5-methyl-isoxazole-4-carboxylic acid Combine the commercial isoxazole, 3-(3-chloro-5-trifluoromethyl-pyririn-2-yl)-5-methyl-isoxazole4-carboxylic acid ethyl ester (490 mg, 1.46 mmol), with aqueous sodium hydroxide (1N, 10.0 mL, 10 mmol), ethanol (2 mL), and tetrahydrofuran (2 mL) and stir overnight at ambient temperature. Adjust the aqueous mixture to approx. pH 2.5 with aqueous hydrochloric acid. Extract with ethyl acetate and dry over sodium sulfate and concentrate in vacuo. Drying nets the desired isoxazole acid in near quantitative yield as an off white solid. MS(ES): $(M+1)^+$ 307.0, 309.0 m/z.

Preparation 39

(3-{[3-(3Chloro-5-trifluoromethyl-pyridin-2-yl)-5-methyl-isoxazole-4-carbonyl]-amino}cyclohexylmethyl)-carbamic acid benzyl ester Combine 3-(3-chloro-5-trifluoromethyl-pyririn-2-yl)-5-methyl-isoxazole-4-carboxylic acid (400 mg, 1.30 mmol) with (3-amino-cyclohexylmethyl)-carbamic acid benzyl ester (389 mg, 1.35 mmol), 1-[3-(dimethyl-amino)propyl]-3-ethylcarbodiimide hydrochloride (250 mg, 1.30 mmol), 1-hydroxy-7-azabenzo-triazole (177 mg, 1.30 mmol), and N,N-diisopropylethyl amine (0.68 mL, 4.27 mmol), in N,N-dimethylformamide (10 mL) and stir overnight at ambient temperature. Concentrate in vacuo and take up in water and extract with ethyl acetate. Dry the combined extracts over sodium sulfate. Concentrate and elute over silica gel using methanol/dichloromethane to give 630 mg (88%) of the desired amide as an off white solid. MS(ES): $(M+1)^+$ 551.0, 553.0 m/z.

Preparation 40

[3-(3-Methyl-4-oxo-7-trifluoromethyl-5H-2-oxa-1,5,9-triaza-cyclopenta[a]naphthalen-5-yl)-cyclohexylmethyl]-carbamic acid benzyl ester Dissolve (3-{[3-(3-chloro-5-trifluoromethyl-pyridin-2-yl)-5-methyl-isoxazole-4-carbonyl]-amino}-cyclohexylmethyl)-carbamic acid benzyl ester (600 mg, 1.09 mmol) in N,N-dimethylformamide (5 mL) at ambient temperature under a nitrogen atmosphere. Add a solution of potassium bis(trimethylsilyl)amide (0.5 M in toluene, 2.62 mL, 1.31 mmol) and stir for 10 min. at ambient temperature. Quench the dark mixture with water and follow by the adding solid sodium chloride. Extract with ethyl acetate and wash with water and dry over sodium sulfate. Concentrate and elute over silica gel with methanol/dichloromethane to give 200 mg (36%) of the desired product as a light foam. MS(ES): $(M+1)^+$ 515.2, 516.2 m/z.

Preparation 41

5-(3-Aminomethyl-cyclohexyl)-3-methyl-7-trifluoromethyl-H-2-oxa-1,5,9-triaza-cyclopenta[a]naphthalen-4-one hydroiodide Dissolve [3-(3-methyl-4-oxo-7-trifluoromethyl-5H-2-oxa-1,5,9-triaza-cyclopenta[a]naphthalen-5-yl)-cyclohexylmethyl]-carbamic acid benzyl ester (200 mg, 0.39 mmol) in dry dichloromethane (10 mL). Add iodotrimethylsilane (0.14 mL, 0.98 mmol) and stir overnight at ambient temperature. Quench the mixture with methanol (5 mL) and concentrate in vacuo. Use the resulting dark crude amine salt directly without purification. MS(ES): $(M+1)^+$ 381.2 m/z.

Preparation 42

3-{[3-(3-Fluoro-pyridin-4-yl)-5-methyl-isoxazole-4-carbonyl]-amino}-cyclohexanecarboxylic acid ethyl ester Dissolve 3-methoxycarbonylamino-cyclohexanecarboxylic acid ethyl ester (513 mg, 2.24 mmol) in dry dichloromethane (10 mL). Add iodotrimethylsilane (0.48 mL, 3.4 mmol) and stir the resulting mixture for 2.5 h at ambient temperature. Quench with methanol (5 mL) and concentrate in vacuo. Concentrate the resulting residue twice from diethyl ether and use the crude amine salt directly without purification. Combine this amine salt with 3-(3-fluoro-pyridin-4-yl)-5-methyl-isoxazole-4-carboxylic acid (500 mg, 2.24 mmol),1-[3-(dimethylamino)-propyl]-3-ethylcarbodiimide hydrochloride (430 mg, 2.24 mmol), 1-hydroxy-7-azabenzo-triazole (305 mg, 2.24 mmol), and N,N-diisopropylethyl amine (2.0 mL, 11.5 mmol) in N,N-dimethylformamide (15 mL) and stir overnight at ambient temperature. Concentrate the mixture in vacuo and take up in water and extract with dichloromethane. Dry the combined extracts over sodium sulfate and concentrate in vacuo. Elute the resulting residue over silica gel using methanol/dichloromethane which to give 720 mg (86%) of the desired amide as a white solid. MS(ES): (M+1)$^+$ 376.2, 377.3 m/z.

Preparation 43

3-(3-Methyl-4-oxo-5H-2-oxa-1,5,7-triaza-cyclopenta[a]naphthalen-5-yl)-cyclohexanecarboxylic acid ethyl ester Dissolve 3-{[3-(3-fluoro-pyridin-4-yl)-5-methyl isoxazole-4-carbonyl]-amino}cyclo-hexanecarboxylic acid ethy ester (0.70 g, 1.87 mmol) in N,N-dimethyl-formamide (10 mL0 at ambient temperature under a nitrogen atmosphere. Add a solution of potassuim bis(trimethylsilyl)amide (0.5 M in toluene, 4.11 mL, 2.06 mmol) and stir for 20 min. at ambient temperature. Quench with water and follow by adding solid sodium chloride. Extract with ethyl acetate and wash the combined extracts with water and dry over sodium sulfate. Concentrate and elute over silica gel using methanol/dichloromethane, allowing for the isolation of 656 mg (99%) of the desired product as a light solid. MS(ES): (M+1)$^+$ 356.2, 357.2 m/z.

Preparation 44

3-(3-Methyl-4-oxo-5H-2-oxa-1,5,7-triaza-cyclopenta[a]naphthalen-5-yl)-cyclohexanecarboxylic acid Combine 3-(3-methyl-4-oxo-5H-2-oxa-1,5,7-triaza-cyclopenta[a]naphthalen-5-yl)-cyclohexane-carboxylic acid ethyl ester (620 mg, 1.75 mmol) with aqueous sodium hydroxide (2N, 5.0 mL, 10.0 mmol), ethanol (2 mL), and tetrahydrofuran (2 mL) and stir at ambient temperature until hydrolysis is complete. Add water and adjust to approx. pH 3.0 with aqueous hydrochloric acid. Extract with dichloromethane and dry over sodium sulfate and concentrate in vacuo to give the desired acid as a tan solid (500 mg, 88%).
MS(ES): (M+1)$^+$ 328.1, 329.1 m/z.

Preparation 45

3,5-dichloropyridine-2-carboxaldehyde

Add a solution of n-butyl lithium (37.5 mL, 0.06 mol, 1.6 M in hexanes) to a mixture of 1,4-diazabicyclo-[2.2.2] octane (6.16 g, 0.055 mol) in diethyl ether (250 mL) at −10 to −20° C. under a nitrogen atmosphere. Stir for 45 min. and then cool to −70° C. Add 3,5-dichloropyridine (7.40 g, 0.05 mol) in small portions and stir for 1.5 h at this temperature. Add N,N-dimethylformamide (7.75 mL, 0.10 mol) dropwise via syringe and stir for 2 h and allow to slowly warm to ~−20° C. Add water (200 mL) is added and extract with ethyl acetate. Dry over sodium sulfate and concentrate in vacuo. Elute over silica gel with hexanes/ethyl acetate to give the desired aldehyde (2.12 g, 49%) as a light yellowish solid. MS(ES): (M+1)$^+$ 174.8, 175.8 m/z.

Preparation 46

3,5-dichloropyridine-2-carboxaldehyde oxime

Combine 3,5-dichloropyridine-2-carboxaldehyde(2.00 g, 0.011 mol) with hydroxylamine hydrochloride (0.81 g, 0.012 mol) and ice (40 g) in an ethanol/water (20 mL/20 mL) mixture. Add aqueous sodium hydroxide (1.16 g, 0.028 mol, in 15 mL of water) dropwise and stir overnight at ambient temperature. Adjust the mixture to approx. pH 7.0 with aqueous hydrochloric acid and extract with ethyl acetate. Dry over sodium sulfate and concentrate in vacuo. Eluted over silica gel using ethyl acetate/dichloromethane to give 1.90 g (88%) of desired oxime as a yellowish solid. MS(ES): (M+1)$^+$ 190.9, 192.9 m/z.

Preparation 47

3-(3,5-Dichloro-pyridin-2-yl)-5-methyl-isoxazole-4-carboxylic acid ethyl ester

Dissolve 3,5-dichloropyridine-2-carboxaldehyde oxime (0.70 g, 0.0037 mol) in N,N-dimethylformamide (10 mL). Add N-chlorosuccinimide (0.55 g, 0.004 mol) in small portions and sitr at ambient temperature until reaction is complete. Pour the mixture into water and extract with ethyl acetate. Wash with water and dry over sodium sulfate. Concentrate in vacuo and use without further purification. Combine this material with ethyl-2-butynoate (6.0 mL, 0.052 mol) under a nitrogen atmosphere. Add triethylamine (3.29 mL, 0.024 mol) in diethyl ether (10 mL) in a dropwise manner and stir overnight at ambient temperature. Quench with water and extract with ethyl acetate. Concentrate and elute over silica gel with dichloromethane to give the desired isoxazole (0.43 g, 39%).
MS(ES): (M+1)$^+$ 301.0, 303.0 m/z.

Preparation 48

3-(3,5-dichloro-pyridin-2-yl)-5-methyl-isoxazole-4-carboxylic acid

Combine 3-(3,5-dichloro-pyridin-2-yl)-5-methyl-isoxazole-4-carboxylic acid ethyl ester (0.755 g, 0.0025 mol) with aqueous sodium hydroxide (2N, 6.0 mL, 0.012 mol), ethanol (2 mL), and tetrahydrofuran (2 mL) and stir overnight at ambient temperature. Add water and adjusted to approx. pH 3.0 with aqueous hydrochloric acid. Extract with ethyl acetate and dry over sodium sulfate and concentrate in vacuo. Drying nets the desired isoxazole acid as a tan solid(0.65 g, 95%). MS (ES): (M+1)$^+$ 273.0,275.0 m/z.

Preparation 49

(3-{[3-(3,5-dichloro-pyridin-2-yl)-5-methyl-isoxazole-4-carbonyl]-amino}-cyclohexylmethyl)-carbamic acid benzyl ester Combine 3-(3,5-dichloro-pyridin-2-yl)-5-methyl-isoxazole-4-carboxylic acid (0.35 g, 0.0013 mol) with (3-aminocyclohexylmethyl)-carbamic acid benzyl ester (0.38 g, 0.0013 mol), 1-[3-(dimethylamino)propyl]-3-ethylcarbodiimide hydrochloride (0.25, 0.0013 mol), 1-hydroxy-7-aza-benzo-triazole (0.18 g, 0.0013 mol), and N,N-diisopropyl-ethyl amine (0.67 mL, 0.0039 mol) in N,N-dimethylformamide (8 mL) and stir overnight at ambient temperature. Concentrate in vacuo and take up in water and extract with dichloromethane. Concentrate and elute over silica gel using ethyl acetate/dichloromethane to give 0.603 g (90%) of the desired amide. MS(ES): (M+1)$^+$ 517.2, 519.2 m/z.

Preparation 50

[3-(7-Chloro-3-methyl-4-oxo-5H-2-oxa-1,5,9-triaza-cyclopenta[a]naphthalen-5-yl)-cyclohexylmethyl]-carbamic acid benzyl ester Dissolve (3-{[3-(3,5-dichloro-pyridin-2-yl)-5-methyl-isoxazole-4-carbonyl]amino}-cyclohexylmethyl acid benzyl ester (600 mg, 1.16 mmol) in N,N-dimethylformamide (10 mL) at ambient temperature under a nitrogen atmosphere. Add a solution of potassium bis(trimethylsilyl)amide (0.5 M in toluene, 2.32 mL, 1.16 mmol) and stir for 20 min. at ambient temperature. Quench with water and follow by adding solid sodium chloride. Extract with ethyl acetate and wash with water and dry over sodium sulfate. Concentrate and elute over silica gel to give 70 mg (12%) of the desired product. MS(ES): (M+1)$^+$ 481.2, 483.2 m/z.

EXAMPLES

Example 1

N-[3-(3-Methyl-4-oxo-5H-2-oxa-1,5,6-triaza-cyclo-penta-[a]naphthalen-5-yl)-cyclohexylmethyl]-nicotinamide Combine 5-(3-aminomethyl-cyclohexyl)-3-methyl-5H-2-oxa-1,5,6-triaza-cyclopenta[a]naphthalen-4-one hydroiodide (200 mg, 0.45 mmol) with nicotinic acid (56 mg, 0.45 mmol), 1-[3-(dimethylamino)propyl]-3-ethylcarbodiimide hydrochloride (87 mg, 0.45 mmol), 1-hydroxy-7-azabenzo-triazole (62 mg, 0.45 mmol), and N,N-diisopropylethyl amine (0.24 mL, 1.38 mmol), in N,N-dimethylformamide (4 mL) and stir over a weekend at ambient temperature. Concentrate in vacuo and take up in water and extract with ethyl acetate. Dry over sodium sulfate and concentrate in vacuo. Elute over silica gel using methanol/dichloromethaneto give 88 mg (47%) of the desired amide as a light tan solid. MS(ES): (M+1)$^+$ 418.2, 419.2 m/z.

Example 2

N-[3-(3-Methyl-4-oxo-5H-2-oxa-1,5,6-triaza-cyclo-penta[a]naphthalen-5-yl)-cyclohexylmethyl]-benzamide Combine 5-(3-aminomethyl-cyclohexyl)-3-methyl-5H-2-oxa-1,5,6-triaza-cyclopenta[a]naphthalen-4-one hydroiodide (100 mg, 0.23 mmol) with benzoic acid (28 mg, 0.23 mmol), 1-[3-(dimethylamino)propyl]-3-ethylcarbodiimide hydrochloride (44 mg, 0.23 mmol), 1-hydroxy-7-azabenzo-triazole (31 mg, 0.23 mmol), and N,N-diisopropylethyl amine (0.12 mL, 0.69 mmol), in N,N-dimethylformamide (4 mL) and stir over a weekend at ambient temperature. Concentrate in vacuo and take up in water and extract with ethyl acetate. Dry over sodium sulfate and concentrate in vacuo. Eluted over silica gel using methanol/dichloromethane to give 72 mg (75%) of the desired amide as an off white solid. MS(ES): (M+1)$^+$ 417.2, 418.2 m/z.

Example 3

N-[3-(3-Methyl-4-oxo-5H-2-oxa-1,5,7-triaza-cyclo-penta[a]naphthalen-5-yl)-cyclohexylmethyl]-benzamide Combine 5-(3-aminomethyl-cyclohexyl)-3-methyl-5H-2-oxa-1,5,7-triaza-cyclopenta[a]naphthalen-4-one hydroiodide (136 mg, 0.31 mmol) with benzoic acid (42 mg, 0.34 mmol), 1-[3-(dimethylamino)propyl]-3-ethylcarbodiimide hydrochloride (65 mg, 0.34 mmol), 1-hydroxy-7-azabenzo-triazole (46 mg, 0.34 mmol), and N,N-diisopropylethyl amine (0.20 mL, 1.15 mmol), in N,N-dimethylformamide (4 mL) and stir over a weekend at ambient temperature. Concentrate in vacuo and take up in water and extract with dichloromethane. Dry over sodium sulfate and concentrate in vacuo. Elute over silica gel using methanol/dichloromethane to give 96 mg (74%) of the desired product as an off white solid. MS(ES): (M+1)$^+$ 417.2, 418.2 m/z.

Example 4

N-[3-(3-Methyl-4-oxo-5H-2-oxa-1,5,7-triaza-cyclo-penta-[a]naphthalen-5-yl)-cyclohexylmethyl]-nicotinamide Combine 5-(3-aminomethyl-cyclohexyl)-3-methyl-5H-2-oxa-1,5,7-triaza-cyclopenta[a]naphthalen-4-one hydroiodide (136 mg, 0.31 mmol) with nicotinic acid (42 mg, 0.34 mmol), 1-[3-(dimethylamino)propyl]-3-ethylcarbodiimide hydrochloride (65 mg, 0.34 mmol), 1-hydroxy-7-azabenzo-triazole (46 mg, 0.34 mmol), and N,N-diisopropylethyl amine (0.20 mL, 1.15 mmol), in N,N-dimethylformamide (4 mL) and stir over a weekend at ambient temperature. Concentrate in vacuo and take up in water and extract with dichloromethane. Dry over sodium sulfate and concentrate in vacuo. Elute over silica gel using methanol/dichloromethane to give 22 mg (17%) of the desired amide as a white solid. MS(EI): Exact Mass Calc'd for: $C_{23}H_{24}N_5O_3$ 418.1879 m/z. Found: 418.1869 m/z.

Example 5

N-[3-(3-Methyl-4-oxo-5H-2-oxa-1,5,8-triaza-cyclo-penta[a]naphthalen-5-yl)-cyclohexylmethyl]-benzamide Combine 5-(3-aminomethyl-cyclohexyl)-3-methyl-5H-2-oxa-1,5,8-triaza-cyclopenta[a]naphthalen-4-one hydroiodide (145 mg, 0.33 mmol) with benzoic acid (44 mg, 0.36 mmol), 1-[3-(dimethylamino)propyl]-3-ethylcarbodiimide hydrochloride (70 mg, 0.36 mmol), 1-hydroxy-7-azabenzo-triazole (49 mg, 0.36 mmol), and N,N-diisopropylethyl amine (0.20 mL, 1.15 mmol), in N,N-dimethylformamide (4 mL) and stir over the weekend at ambient temperature. Concentrate in vacuo and take up in water and extract with dichloromethane. Dry over sodium sulfate and concentrate in vacuo. Elute over silica gel using methanol/dichloromethane to give 98 mg (71%) of the desired product as a white solid. MS(ES): (M+1)$^+$ 417.0, 418.1 m/z.

Example 6

N-[3-(3-Methyl-oxo-5H-2-oxa-1,5,8-triaza-cyclo-penta-[a]naphthalen-5-yl)-cyclohexylmethyl]-nicotinamide Combine 5-(3-aminomethyl-cyclohexyl)-3-methyl-5H-2-oxa-1,5,8-triaza-cyclopenta[a]naphthalen-4-one hydroiodide (145 mg, 0.31 mmol) with nicotinic acid (45 mg, 0.36 mmol), 1-[3-(dimethylamino)propyl]-3-ethylcarbodiimide hydrochloride (70 mg, 0.36 mmol), 1-hydroxy-7-azabenzotriazole (49 mg, 0.36 mmol), and N,N-diisopropylethyl amine (0.20 mL, 1.15 mmol), in N,N-dimethylformamide (4 mL) and stir over a weekend at ambient temperature. Concentrate in vacuo and take up in water and extract with dichloromethane. Dry over sodium sulfate and concentrate in vacuo. Eluted over silica gel using methanol/dichloromethane to give 115 mg (83%) of the desired amide as a solid. MS(ES): $(M+1)^+$ 418.0,419.0 m/z.

Example 7

N-[3-(9-Chloro-3-methyl-4-oxo-5H-2-oxa-1,5,7-triaza-cyclopenta[a]naphthalen-5-yl)cyclohexylmethyl]-benzamide Dissolve [3-(9-chloro-3-methyl-4-oxo-5H-2-oxa-1,5,7-triaza-cyclopenta[a]naphthalen-5-yl)-cyclohexylmethyl]-carbamic acid benzyl ester (310 mg, 0.64 mmol) in dry dichloromethane (8 mL). Add iodotrimethylsilane (0.23 mL, 1.62 mmol) and stir overnight at ambient temperature. Quench with methanol (5 mL) and concentrate in vacuo. Concentrate twice from diethyl ether and use the dark solid crude amine salt directly without purification. MS(ES): $(M+1)^+$ 347.1 m/z. Combine this amine salt with benzoic acid (94 mg, 0.77 mmol),1-[3-(dimethylamino)-propyl]-3-ethylcarbodiimide hydrochloride (148 mg, 0.77 mmol), 1-hydroxy-7-azabenzo-triazole (105 mg, 0.77 mmol), and N,N-diisopropylethyl amine (0.45 mL, 2.59 mmol), in N,N-dimethylformamide (8 mL) and stir over a weekend at ambient temperature. Concentrate in vacuo and take up in water and extract with dichloromethane. Dry over sodium sulfate and concentrate in vacuo. Elute over silica gel using methanol/dichloromethane to give 74 mg (26%) of the desired product as a white solid. MS(ES): $(M+1)^+$ 451.1, 453.1 m/z.

Example 8

N-[3-(3-Methyl-4-oxo-5H-2-oxa-1,5,9-triaza-cyclopenta[a]naphthalen-5-yl)-cyclohexylmethyl]-benzamide Dissolve [3-(3-methyl-4-oxo-5H-2-oxa-1,5,9-triaza-cyclopenta[a]naphthalen-5yl)-cyclohexylmethyl]-carbamic acid benzyl ester (130 mg, 0.29 mmol) in dry dichloromethane (5 mL). Add iodotrimethylsilane (0.11 mL, 0.77 mmol) and stir overnight at ambient temperature. Quench with methanol (5 mL) and concentrate in vacuo. Dissolve in minimal dichloromethane and add excess diethyl ether. Decant and dry the dark solid crude amine salt in vacuo and use directly without purification. MS(ES): $(M+1)^+$ 313.1, 314.1 m/z. Combine this amine salt with benzoic acid (36 mg, 0.29 mmol),1-[3-(dimethylamino)-propyl]-3-ethylcarbodiimide hydrochloride (56 mg, 0.29 mmol), 1-hydroxy-7-azabenzo-triazole (40 mg, 0.29 mmol), and N,N-diisopropylethyl amine (0.20 mL, 1.15 mmol), in N,N-dimethylformamide (5 mL) and stir overnight at ambient temperature. Concentrated in vacuo and take up in water and extract with dichloromethane. Dry over sodium sulfate and concentrate in vacuo. Elute over silica gel using methanol-dichloromethane to give 97 mg (80%) of the desired product as a light tan solid. MS(ES): $(M+1)^+$ 417.1, 418.1 m/z.

Example 9

N-[3-(3-Methyl-4-oxo-7-trifluoromethyl-5H-2-oxa-1,5,9-triaza-cyclopenta[a]naphthalen-5-yl)-cyclohexylmethyl]-benzamide Combine 5-(3-aminomethyl-cyclohexyl)-3-methyl-7-trifluoromethyl-5H-2-oxa-1,5,9-triaza-cyclopenta[a]nephthalen-4-one hydroiodide (0.39 mmol) with benzoic acid (57 mg, 0.47 mmol), 1-[3-(dimethylamino)propyl]-3-ethylcarbodiimide hydrochloride (90 mg, 0.47 mmol), 1-hydroxy-7-azabenzo-triazole (63 mg, 0.47 mmol), and N,N-diisopropylethyl amine (0.27 mL, 1.55 mmol), in N,N-dimethylformamide (5 mL) and stir over a weekend at ambient temperature. Concentrate in vacuo and take up in water and extract with dichloromethane. Dry over sodium sulfate and concentrate in vacuo. Elute over silica gel using 1% methanol/dichloromethane to give 74 mg (39%) of the desired product as a white solid. MS(ES): $(M+1)^+$ 485.0, 486.1 m/z.

Example 10

N-[3-(3-Methyl-4-oxo-7-trifluoromethyl-5H-2-oxa-1,5,9-triaza-cyclopenta[a]naphthalen-5-yl)-cyclohexylmethyl]-nicotinamide Combine 5-(3-aminomethyl-cyclohexyl)-3-methyl-7-trifluoromethyl-5H-2-oxa-1,5,9-triaza-cyclopenta[a]naphthalen-4-one hydroiodide (0.19 mmol) with nicotinic acid (27 mg, 0.22 mmol), 1-[3-(dimethylamino)propyl]-3-ethylcarbodiimide hydrochloride (43 mg, 0.22 mmol), 1-hydroxy-7-azabenzo-triazole (30 mg, 0.22 mmol), and N,N-diisopropylethyl amine (0.10 mL, 0.56 mmol), in N,N-dimethylformamide (4 mL) and stir overnight at ambient temperature. Concentrate in vacuo and take up in water and extract with ethyl acetate. Dry over sodium sulfate and concentrate in vacuo. Elute over silica gel using methanol/dichloromethane to give 62 mg (69%) of the desired amide as a white solid. MS(ES): $(M+1)^+$ 486.1, 487.2 m/z.

Example 11

3-(3-Methyl-4-oxo-5H-2-oxa-1,5,7-triaza-cyclopenta[a]naphthalen-5-yl)-cyclohexanecarboxylic acid 3,4,5-trimethoxy-benzylamide Combine 3-(3-methyl-4-oxo-5H-2-oxa-1,5,7-triaza-cyclopenta[a]naphthalen-5-yl)-cyclohexanecarboxylic acid (50 mg, 0.15 mmol) with 1-[3-(dimethyl-amino)propyl]-3-ethylcarbodiimide hydrochloride (32 mg, 0.17 mmol), 1-hydroxy-7-azabenzo-triazole (23 mg, 0.17 mmol), N,N-diisopropylethyl amine (44 mg, 3.4 mmol) and 3,4,5-trimethoxy benzylamine (33 mg, 0.17 mmol) in N,N-dimethyl-formamide (4 mL) and stir overnight at ambient temperature. Concentrate in vacuo and take up in water and extract with dichloromethane. Dry the combined extracts over sodium sulfate. Concentrate and chromatograph over silica gel to give 66 mg (85%) of the desired product as a white solid. MS(ES): $(M+1)^+$ 507.2, 508.2, 509.2 m/z.

Example 12

3-(3-Methyl-4-oxo-5H-2-oxa-1,5,7-triaza-cyclopenta [a]naphthalen-5-yl)-cyclohexanecarboxylic acid benzylamide Combine 3-(3-methyl-4-oxo-5H-2-oxa-1,5,7-triaza-cyclopenta[a]naphthalen-5-yl)-cyclohexanecarboxylic acid (50 mg, 0.15 mmol) with 1-[3-(dimethyl-amino)propyl]-3ethylcarbodiimide hydrochloride (32 mg, 0.17 mmol), 1-hydroxy-7-azabenzo-triazole (23 mg, 0.17 mmol), N,N-diisopropylethyl amine (44 mg, 3.4 mmol), and benzylamine (18 mg, 0.17 mmol) in N,N-dimethyl-formamide (4 mL) and stir overnight at ambient temperature. Concentrate in vacuo and take up in water and extract with dichloromethane. Dry the combined extracts over sodium sulfate. Concentrate and elute over silica gel using methanol/dichloromethane to give 60 mg (94%) of the desired product as a white solid. MS(ES): $(M+1)^+$ 417.3, 418.3 m/z.

Example 13

N-[3-(7-Chloro-3-methyl-4-oxo-5H-2-oxa-1,5,9-triaza-cyclopenta[a]naphthalen-5-yl)-cyclohexylmethyl]-benzamide Dissolve [3-(7-chloro-3-methyl-4-oxo-5H-2-oxa-1,5,9-triaza-cyclopenta[a]naphthalen-5-yl)-cyclohexylmethyl]-carbamic acid benzyl ester(70 mg, 0.15 mmol) in dry dichloromethane (5 mL). Add iodotrimethylsilane (0.05 mL, 0.35 mmol) and stir overnight at ambient temperature. Quench with methanol (5 mL) and concentrate in vacuo. Concentrate the resulting residue twice from diethyl ether and use directly without purification. Combine this amine salt with benzoic acid (22 mg, 0.18 mmol), 1-[3-(dimethylamino)-propyl]-3-ethylcarbodiimide hydrochloride (34 mg, 0.18 mmol), 1-hydroxy-7-azabenzo-triazole (24 mg, 0.18 mmol), and N,N-diisopropylethyl amine (0.10 mL, 0.57 mmol) in N,N-dimethylformamide (5 mL) and stir over a weekend at ambient temperature. Concentrate in vacuo and take up in water and extract with ethyl acetate. Dry the combined extracts over sodium sulfate and concentrate in vacuo. Elute the resulting residue over silica gel using ethyl acetate/dichloromethane to give 26 mg (38%) of the desired product as a white solid. MS(ES): $(M+1)^+$ Exact Mass Calc'd: 451.1537. Found: 451.1554 m/z.

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Vincristine, epirubicin, daunorubicin, doxorubicin, and etoposide are examples of oncolytics that are substrates of MRP1. See Cole, et. al., "Pharmacological Characterization of Multidrug Resistant MRP-transfected Human Tumor Cells", *Cancer Research*, 54:5902–5910, 1994. Since MRP1 is ubiquitous in mammals, particularly humans, Nooter, K, et. al., "Expression of the Multidrug Resistance-Associated Protein (MRP) Gene in Human Cancers", *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay which rapidly and accurately measured the activity of the tested compound in inhibiting MRP1 or MDR1. Assays useful for evaluating this reversing capability are well known in the art. See, e.g., T. McGrath, et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., *Cancer Research*, 54: 5902–5910, 1994.

Assay for Reversal of MRP1-Mediated Doxorubicin Resistance and MDR1-Mediated Vincristine Resistance: HL60/ADR and HL60/VCR are continuous cell lines, which were selected for doxorubicin and vincristine resistance respectively by culturing HL60, a human acute myeloblastic leukemia cell line, in increasing concentrations of doxorubicin or vincristine until a highly resistant variant was attained.

HL60/ADR and L60/VCR cells were grown in RPMI 1640 (Gibco) containing 10% fetal bovine serum (FBS) and 250 µg/ml GENTAMICIN™ (Sigma). Cells were harvested; washed twice with assay medium (same as culture media); counted; and diluted to $2 \times 10^5$ cells/ml in assay medium. Fifty microliters of cells were aliquoted into wells of a 96 well tissue culture plate. One column of each 96 well plate served as a negative control and received assay medium containing no cells.

Test compounds and reference compounds were dissolved in dimethyl sulfoxide (DMSO) at a concentration of 5 mM. Samples were diluted to 20 µM in assay medium and 25 µl of each test compound was added to 6 wells. Assay standards were run in quadruplicate. Twenty-five microliters of 0.4% DMSO was added to four wells as a solvent control. Assay media was added to all wells to achieve a final volume of 100 µl per well.

The plates were incubated at 37° C. for 72 hours in a humidified incubator with a 5% carbon dioxide atmosphere. Cell viability and vitality was measured by oxidation of a tetrazolium salt using standard conditions. The plates were incubated for 3 hours at 37° C. Absorbance was determined at 490 nm using a microtitre plate reader.

The ability of a test compound to reverse the resistance of HL60/ADR and HL60/VCR cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration does not usually inhibit the growth of HL60/ADR or HL60/VCR cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/ADR cell line over the HL60/VCR cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645-1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices which deliver the formulation in an appropriate manner.

The following formulation examples are illustrative only and are not intended to limit the scope of the invention in any way. "Active ingredient(s)" means a compound according to formula I or a pharmaceutical salt or solvate thereof optionally with one or more oncolytics.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of formula I:

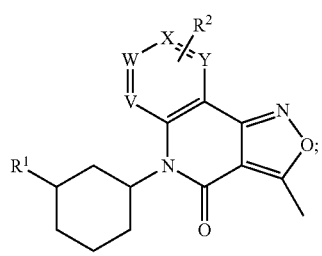

wherein:
any one of V, W, X, or Y is nitrogen, and the others are carbon;
$R^1$ is $NHR^3$, $CH_2NHR^3$, $CH_2C(O)NHR^4$, or $C(O)NHR^4$;
$R^2$ is hydrogen, halo, or trifluoromethyl;
$R^3$ is $C(O)OR^5$ or $C(O)R^6$;
$R^4$ is optionally substituted phenyl or $CH_2$-(optionally substituted phenyl);
$R^5$ is optionally substituted phenyl, optionally substituted heterocycle, or CH(OH)-(optionally substituted phenyl);
$R^6$ is optionally substituted phenyl, optionally substituted heterocycle, or CH(OH)-(optionally substituted phenyl); or a pharmaceutical salt thereof.

2. A method of inhibiting MRP1 in a mammal which comprises administering to a mammal in need thereof an effective amount of a compound of formula I:

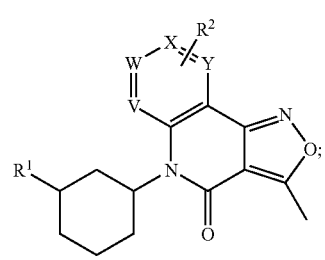

wherein:
any one of V, W, X, or Y is nitrogen, and the others are carbon;
$R^1$ is $NHR^3$, $CH_2NHR^3$, $CH_2C(O)NHR^4$, or $C(O)NHR^4$;
$R^2$ is hydrogen, halo, or trifluoromethyl;
$R^3$ is $C(O)OR^5$ or $C(O)R^6$;
$R^4$ is optionally substituted phenyl or $CH_2$-(optionally substituted phenyl);
$R^5$ is optionally substituted phenyl, optionally substituted heterocycle, or CH(OH)-(optionally substituted phenyl);
$R^6$ is optionally substituted phenyl, optionally substituted heterocycle, or CH(OH)-(optionally substituted phenyl); or a pharmaceutical salt thereof.

3. The method according to claim 2 where the mammal is a human.

4. A method of inhibiting a resistant neoplasm, or a neoplasm susceptible to resistance, in a mammal which comprises administering to a mammal in need thereof an effective amount of a compound of formula I:

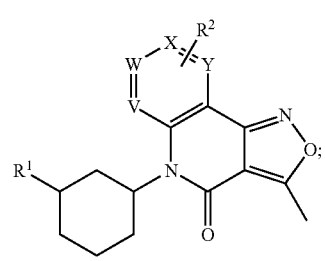

wherein:
any one of V, W, X, or Y is nitrogen, and the others are carbon;
$R^1$ is $NHR^3$, $CH_2NHR^3$, $CH_2C(O)NHR^4$, or $C(O)NHR^4$;
$R^2$ is hydrogen, halo, or trifluoromethyl;
$R^3$ is $C(O)OR^5$ or $C(O)R^6$;
$R^4$ is optionally substituted phenyl or $CH_2$-(optionally substituted phenyl);

R⁵ is optionally substituted phenyl, optionally substituted heterocycle, or CH(OH)-(optionally substituted phenyl);

R⁶ is optionally substituted phenyl, optionally substituted heterocycle, or CH(OH)-(optionally substituted phenyl); or a pharmaceutical salt thereof;

in combination with an effective amount of one or more oncolytic agents.

5. The method according to claim 4 where the mammal is a human.

6. The method according to claim 5 where the oncolytic(s) is selected from: doxorubicin, daunorubicin, epirubicin, vincristine, and etoposide.

7. The method according to claim 6 where the neoplasm is of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, and bronchogenic carcinoma.

8. A pharmaceutical formulation comprising a compound of formula I:

[Chemical structure I]

wherein:
any one of V, W, X, or Y is nitrogen, and the others are carbon;
$R^1$ is $NHR^3$, $CH_2NHR^3$, $CH_2C(O)NHR^4$, or $C(O)NHR^4$;
$R^2$ is hydrogen, halo, or trifluoromethyl;
$R^3$ is $C(O)OR^5$ or $C(O)R^6$;
$R^4$ is optionally substituted phenyl or $CH_2$-(optionally substituted phenyl);
$R^5$ is optionally substituted phenyl, optionally substituted heterocycle, or CH(OH)-(optionally substituted phenyl);
$R^6$ is optionally substituted phenyl, optionally substituted heterocycle, or CH(OH)-(optionally substituted phenyl); or a pharmaceutical salt thereof;

in combination with one or more pharmaceutical carriers, diluents, or excipients therefor.

9. A pharmaceutical formulation comprising:
(a) a compound of formula I:

[Chemical structure I]

wherein:
any one of V, W, X, or Y is nitrogen, and the others are carbon;
$R^1$ is $NHR^3$, $CH_2NHR^3$, $CH_2C(O)NHR^4$, or $C(O)NHR^4$;
$R^2$ is hydrogen, halo, or trifluoromethyl;
$R^3$ is $C(O)OR^5$ or $C(O)R^6$;
$R^4$ is optionally substituted phenyl or $CH_2$-(optionally substituted phenyl);
$R^5$ is optionally substituted phenyl, optionally substituted heterocycle, or CH(OH)-(optionally substituted phenyl);
$R^6$ is optionally substituted phenyl, optionally substituted heterocycle, or CH(OH)-(optionally substituted phenyl); or a pharmaceutical salt thereof;
(b) one or more oncolytic agents; and
(c) one or more pharmaceutical carriers, diluents, or excipients therefor.

10. The formulation according to claim 9 where the oncolytic(s) is selected from: doxorubicin, daunorubicin, epirubicin, vincristine, and etoposide.

\* \* \* \* \*